United States Patent
Gupta et al.

(10) Patent No.: US 10,395,362 B2
(45) Date of Patent: Aug. 27, 2019

(54) CONTOUR BASED DEFECT DETECTION

(71) Applicant: KLA-Tencor Corporation, Milpitas, CA (US)

(72) Inventors: Ajay Gupta, Santa Clara, CA (US); Mohan Mahadevan, Livermore, CA (US); Sankar Venkataraman, Milpitas, CA (US); Hedong Yang, Santa Clara, CA (US); Laurent Karsenti, Rehovot (IL); Yair Carmon, Stanford, CA (US); Noga Bullkich, Brookline, MA (US); Udy Danino, Givat Shmuel (IL)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/896,060

(22) Filed: Feb. 14, 2018

(65) Prior Publication Data
US 2018/0293721 A1    Oct. 11, 2018

Related U.S. Application Data

(60) Provisional application No. 62/483,223, filed on Apr. 7, 2017.

(51) Int. Cl.
G06T 7/00 (2017.01)
G06T 7/564 (2017.01)
(Continued)

(52) U.S. Cl.
CPC ......... *G06T 7/001* (2013.01); *G01N 21/8851* (2013.01); *G01N 21/9501* (2013.01);
(Continued)

(58) Field of Classification Search
CPC ........... G01N 21/9501; G01N 21/8851; G01N 21/95607; G01N 2021/8887; G06T 2207/30148; G06T 7/001; G06T 7/564
(Continued)

(56) References Cited

U.S. PATENT DOCUMENTS 7,570,796 B2    8/2009 Zafar et al.
7,676,077 B2    3/2010 Kulkarni et al.
(Continued)

OTHER PUBLICATIONS

Ding et al., "Machine Learning based Lithographic Hotspot Detection with Critical-Feature Extraction and Classification," Conference: IC Design and Technology, 2009, ICICDT '09, Jun. 2009, 4 pages.
Gao et al., "Lithography Hotspot Detection and Mitigation in Nanometer VLSI," 2013 IEEE 10th International Conference on ASIC, Oct. 2013, 4 pages.
Hand et al., "Principles of Data Mining (Adaptive Computation and Machine Learning)," MIT Press, Aug. 1, 2001, 578 pages.
He et al., "Deep Residual Learning for Image Recognition," arXiv:1512.03385v1, Dec. 10, 2015, 12 pages.
(Continued)

*Primary Examiner* — Tri T Ton
(74) *Attorney, Agent, or Firm* — Ann Marie Mewherter

(57) ABSTRACT

Methods and systems for detecting defects in patterns formed on a specimen are provided. One system includes one or more components executed by one or more computer subsystems, and the component(s) include first and second learning based models. The first learning based model generates simulated contours for the patterns based on a design for the specimen, and the simulated contours are expected contours of a defect free version of the patterns in images of the specimen generated by an imaging subsystem. The second learning based model is configured for generating actual contours for the patterns in at least one acquired image of the patterns formed on the specimen. The computer subsystem(s) are configured for comparing the actual contours to the simulated contours and detecting defects in the patterns formed on the specimen based on results of the comparing.

27 Claims, 7 Drawing Sheets

(51) Int. Cl.
  *G01N 21/95* (2006.01)
  *G01N 21/88* (2006.01)
  *G01N 21/956* (2006.01)

(52) U.S. Cl.
  CPC ....... *G01N 21/95607* (2013.01); *G06T 7/564* (2017.01); *G01N 2021/8887* (2013.01); *G06T 2207/10061* (2013.01); *G06T 2207/20081* (2013.01); *G06T 2207/20084* (2013.01); *G06T 2207/30148* (2013.01)

(58) Field of Classification Search
  USPC .................. 356/237.1–237.6, 239.1–239.8
  See application file for complete search history.

(56) References Cited

U.S. PATENT DOCUMENTS

| | | |
|---|---|---|
| 8,126,255 B2 | 2/2012 | Bhaskar et al. |
| 8,611,637 B2 | 12/2013 | Shi et al. |
| 8,664,594 B1 | 4/2014 | Jiang et al. |
| 8,692,204 B2 | 4/2014 | Kojima et al. |
| 8,698,093 B1 | 4/2014 | Gubbens et al. |
| 8,716,662 B1 | 5/2014 | MacDonald et al. |
| 9,222,895 B2 | 12/2015 | Duffy et al. |
| 2008/0130982 A1* | 6/2008 | Kitamura ............. G06K 9/00 382/144 |
| 2009/0037134 A1 | 2/2009 | Kulkarni et al. |
| 2015/0324963 A1 | 11/2015 | Sezginer et al. |
| 2017/0148226 A1 | 5/2017 | Zhang et al. |
| 2017/0193680 A1 | 7/2017 | Zhang et al. |
| 2017/0194126 A1 | 7/2017 | Bhaskar et al. |
| 2017/0200260 A1 | 7/2017 | Bhaskar et al. |
| 2017/0200265 A1 | 7/2017 | Bhaskar et al. |
| 2017/0345140 A1 | 11/2017 | Zhang et al. |

OTHER PUBLICATIONS

International Search Report for PCT/US2018/025307 dated Jul. 16, 2018.
Jebara, "Discriminative, Generative, and Imitative Learning," MIT Thesis, Feb. 2002, 212 pages.
Krizhevsky et al., "ImageNet Classification with Deep Convolutional Neural Networks," NIPS, Jan. 2012, 9 pages.
Makhzani et al., "Adversarial Autoencoders," arXiv:1511.05644v2, May 25, 2016, 16 pages.
Shin et al., "CNN Based Lithography Hotspot Detection," International Journal of Fuzzy Logic and Intelligent Systems 2016, vol. 16, No. 3, Sep. 2016, pp. 208-215.
Simonyan et al., "Very Deep Convolutional Networks for Large-Scale Image Recognition," presented at International Conference on Learning Representations (ICLR) 2015, Apr. 10, 2015, 14 pages.
Sugiyama, "Introduction to Statistical Machine Learning," Morgan Kaufmann, Oct. 9, 2015, 534 pages.
Szegedy et al., "Going Deeper with Convolutions," 2015 IEEE Conference on Computer Vision and Pattern Recognition (CVPR), Jun. 2015, 9 pages.
Takada et al., "Defect Detection and Classification of Electronic Circuit Boards Using Keypoint Extraction and CNN Features," Patterns 2017: The Ninth International Conferences on Pervasive Patterns and Applications, Feb. 19, 2017, pp. 114-116.
U.S. Appl. No. 15/694,719, filed Sep. 1, 2017 by Zhang et al. (submitted as U.S. Patent Application Publication No. 2018/0107928 published Apr. 19, 2018).
U.S. Appl. No. 15/697,426, filed Sep. 6, 2017 by He et al.
Xie et al., "Holistically-Nested Edge Detection," Department of Computer Science and Engineering, UC San Diego, arXiv: 1504.06375v2, Oct. 4, 2015, 10 pages.
Yang et al., Imbalance Aware Lithography Hotspot Detection: A Deep Learning Approach, Journal of Micro/Nanolithography, MEMS, and MOEMS, 16(3), Jul.-Sep. 2017, 13 pages.

\* cited by examiner

CONTOUR BASED DEFECT DETECTION

BACKGROUND OF THE INVENTION

1. Field of the Invention

The present invention generally relates to methods and systems for detecting defects in patterns formed on a specimen.

2. Description of the Related Art

The following description and examples are not admitted to be prior art by virtue of their inclusion in this section.

Inspection processes are used at various steps during a semiconductor manufacturing process to detect defects on wafers to drive higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Defect review typically involves re-detecting defects detected as such by an inspection process and generating additional information about the defects at a higher resolution using either a high magnification optical system or a scanning electron microscope (SEM). Defect review is therefore performed at discrete locations on the wafer where defects have been detected by inspection. The higher resolution data for the defects generated by defect review is more suitable for determining attributes of the defects such as profile, roughness, more accurate size information, etc. Since the defect review is performed for defects detected on the wafer by inspection, the parameters used for defect review at a location of a detected defect may be determined based on attributes of the defects determined by the inspection process.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined using currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at which a metrology process is performed on a wafer may be independent of the results of an inspection process performed on the wafer. In particular, the locations at which a metrology process is performed may be selected independently of inspection results. In addition, since locations on the wafer at which metrology is performed may be selected independently of inspection results, unlike defect review in which the locations on the wafer at which defect review is to be performed cannot be determined until the inspection results for the wafer are generated and available for use, the locations at which the metrology process is performed may be determined before an inspection process has been performed on the wafer.

Measuring critical dimensions (CDs) of "key" structures is vital to process monitoring in current and next generation nodes (e.g., 7 nm and 5 nm). The determination of "key" comes from several sources such as known rules of density and proximity, simulation, experience, and optical proximity correction (OPC) among others. However, a SEM image is able to see pattern fidelity irrespective of these priors and can help identify unknown "hot spots" without an explicit need for these priors, which can be extremely valuable for process control but also potentially open new characterization methodologies for pattern fidelities.

Currently used methods for CD-SEMs have several challenges such as that they are slow, they require careful setup for each site and a knowledge of which sites to measure, and their results need to be interpreted further downline. The use of substantially fast review SEMs is gaining popularity to cover this fidelity application. In addition, it allows customers to develop and use their own algorithm solutions reducing these platforms as "image takers." Therefore, the need is clear to overcome these challenges to enable adequate pattern fidelity monitoring for users.

Typical CD measurement applications include a number of modules. One such module is region of interest (ROI) definition that includes identification and marking of areas where CD measurements are to he taken. Another such module includes an optional design rendering step which includes generating expected SEM contours from pre-OPC design. An additional module includes edge extraction that includes generating edges and/or contours from current SEM images. A further such module includes measurement algorithms that include comparing expected and current "edges" within the defined ROI.

There have been several previous attempts to cover these steps. The main challenges of these previous attempts lie in heuristic determination of contours which can fail for complex patterns and pattern intersections. These attempts also lack robustness to imaging conditions and require parameter tweaking for noisy and soft images. Therefore, any method must overcome these limitations as much as possible if we are to generically explore any random pattern for pattern fidelity.

For pattern hot spot detection, currently used methods employ both learning and non-learning based methods (i.e., use hand crafted algorithms). Some of these methods try to detect hot spots using learning based algorithms with CAD data only (no images) as input and trying to predict/classify whether a given pattern is a hot spot or not. Other methods use both CAD and image (SEM or optical) data and predict/classify whether a detected defect is a hot spot or not manually or using hand crafted features or learning based features. However, none of these methods quantify these hot spots by reporting a CD metric which is required in order to accurately determine a hot spot based on the user-defined threshold.

The currently used methods for hot spot detection have a number of disadvantages. For example, the currently used methods have no flexibility to automatically adapt to different pattern types (i.e., memory or logic). In addition, the currently used methods have no generalization to different image modalities. In an additional example, the currently used methods require hand crafted (heuristics) models of image modalities to characterize pattern variation and bias. In a further example, the currently used methods provide no quantitative pattern characterization and hot spot detection. Instead, the currently used methods report CD or other pattern fidelity metrics for the entire field of view from a single shot measurement. In yet another example, the currently used methods provide no ability to handle OPC errors naturally without having to handle each kind of OPC error heuristically.

Accordingly, it would be advantageous to develop systems and methods for detecting defects in patterns formed on a specimen that do not have one or more of the disadvantages described above.

SUMMARY OF THE INVENTION

The following description of various embodiments is not to be construed in any way as limiting the subject matter of the appended claims.

One embodiment relates to a system configured to detect defects in patterns formed on a specimen. The system includes an imaging subsystem that includes at least an energy source and a detector. The energy source is configured to generate energy that is directed to a specimen. The detector is configured to detect energy from the specimen and to generate images responsive to the detected energy. The system also includes one or more computer subsystems configured for acquiring the images of patterns formed on the specimen. In addition, the system includes one or more components executed by the one or more computer subsystems. The one or more components include a first learning based model and a second learning based model. The first learning based model is configured for generating simulated contours for the patterns based on a design for the specimen input to the first learning based model by the one or more computer subsystems. The simulated contours are expected contours of a defect free version of the patterns in the images of the specimen generated by the imaging subsystem. The second learning based model is configured for generating actual contours for the patterns in at least one of the acquired images of the patterns formed on the specimen input to the second learning based model by the one or more computer subsystems. The one or more computer subsystems are configured for comparing the actual contours to the simulated contours and detecting defects in the patterns formed on the specimen based on results of the comparing. The system may be further configured as described herein.

Another embodiment relates to a computer-implemented method for detecting defects in patterns formed on a specimen. The method includes acquiring images of patterns formed on a specimen by an imaging subsystem with one or more computer subsystems. The imaging subsystem is configured as described above. The method also includes generating simulated contours for the patterns based on a design for the specimen input to a first learning based model by the one or more computer subsystems. The simulated contours are those described above. In addition, the method includes generating actual contours for the patterns in at least one of the acquired images of the patterns formed on the specimen input to a second learning based model by the one or more computer subsystems. One or more components are executed by the one or more computer subsystems. The one or more components include the first and second learning based models. The method also includes comparing the actual contours to the simulated contours and detecting defects in the patterns formed on the specimen based on results of the comparing. The steps of the method are performed by one or more computer systems.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for detecting defects in patterns formed on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other steps) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
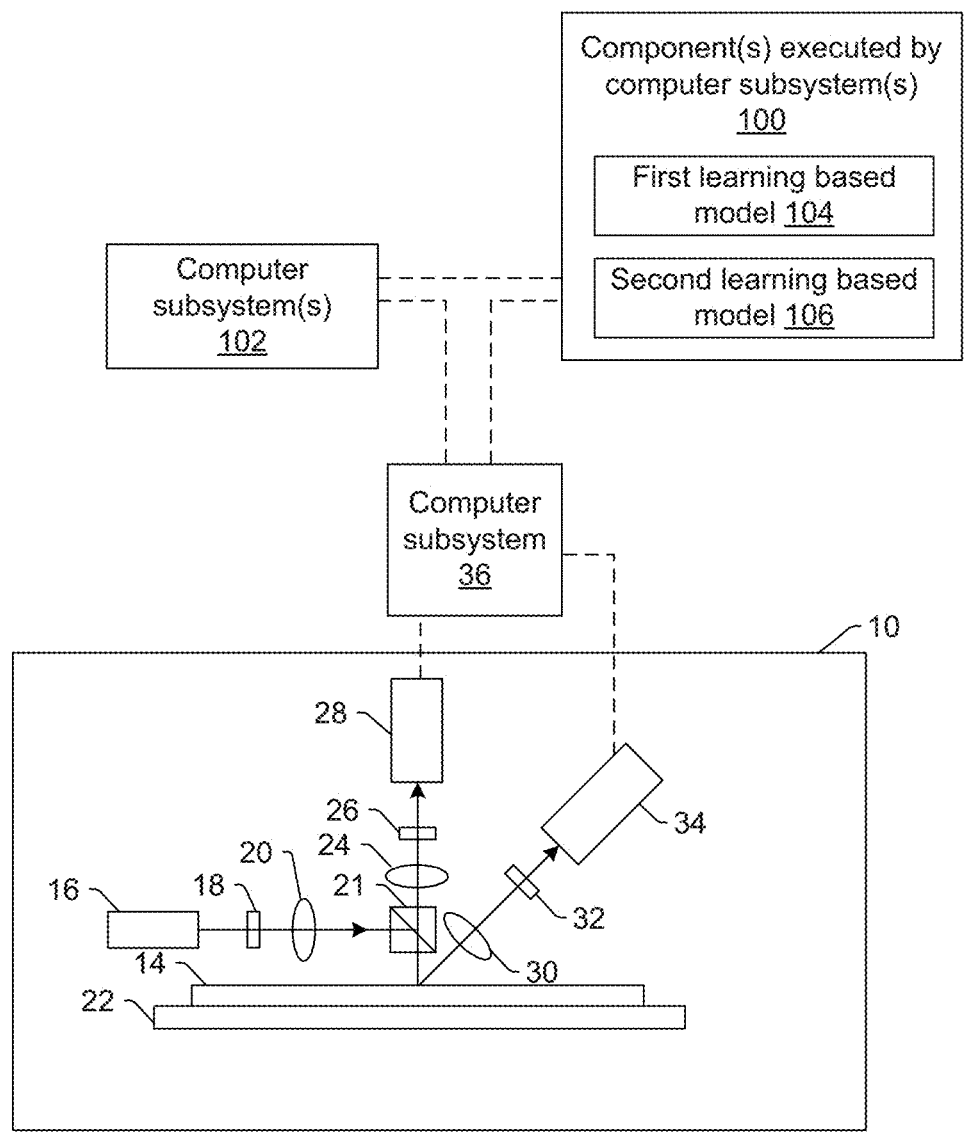
FIGS. 1 and 2 are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. The physical design may be stored in a data structure such as a graphical data stream (GDS) file, any other standard machine-readable file, any other suitable file known in the art, and a design database. A GDSII file is one of a class of files used for the representation of design layout data. Other examples of such files include GL1 and OASIS files and proprietary. file formats such as RDF data, which is proprietary to KLA-Tencor, Milpitas, Calif. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In some instances, simulated or acquired images from a wafer or reticle can be used as a proxy for the design. Image analysis can also be used as a proxy for design analysis. For example, polygons in the design may be extracted from an image of a design printed on a wafer and/or reticle, assuming that the image of the wafer and/or reticle is acquired with sufficient resolution to adequately image the polygons of the design. In addition, the "design" and "design data" described herein refers to information and data that is generated by semiconductor device designers in a design process and is therefore available for use in the embodiments described herein well in advance of printing of the design on any physical wafers.

Preferably, the "design" or "physical design" as those terms are used herein refer to the design as it would be ideally formed on the wafer. In this manner, a design or physical design described herein would preferably not include features of the design that would not be printed on the wafer such as optical proximity correction (OPC) features, which are added to the design to enhance printing of the features on the wafer without actually being printed themselves. In this manner, in some embodiments, the design for the specimen used for the steps described further herein does not include features of the design that will not be printed on the specimen.

A "design" and "design data" described herein may include data and information related to the physical intent for the device being formed on the wafer, which may include any of the various types of design and design data described above. A "design" and "design data" may also or alternatively include data and information related to the electrical intent for the device being formed on the wafer. Such information and data may include, for example, netlist and SPICE nomenclature and/or an "annotated layout" (e.g., where the design includes electrical netlist parameter labeling). Such data and information may be used to determine which parts of a layout or wafer image are critical in one or more electrical aspects.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects in patterns formed on a specimen. In one embodiment, the specimen includes a wafer. In another embodiment, the specimen includes a reticle. The wafer and the reticle may include any wafer and reticle known in the art.

In general, the embodiments described herein are capable of robust and generalized pattern fidelity measurements using deep learning. For example, as described further herein, the embodiments described herein provide data driven approaches to automatically characterize patterns printed on semiconductor wafers and other specimens while ignoring stochastic process noise. In addition, the embodiments described herein provide a data driven, learning-based, generalized, quantitative pattern characterization method that can be generally applied to semiconductor images acquired from different kinds of modalities including optical, scanning electron microscope (SEM), etc. Semiconductor process control for current and next generation nodes requires unprecedented monitoring of pattern fidelity in addition to the usual mode of defect-based process control. While critical dimension (CD) SEMs offer the ability to make measurements on specific types of structures, they have several challenges: (1) they are relatively slow; (2) they require careful setup for each site and a knowledge of which sites to measure; and (3) their results need to be interpreted further downline. Furthermore, other challenges that exist when working with SEM images are that shot noise, charging, streaking, and soft edges that can throw off standard image processing methods or may require heuristics to deal with them.

The embodiments described herein are based, at least in part, on a deep learning based approach that can generically analyze a SEM image either with design as a reference or another die as a reference and return two key pieces of information: (1) location of outliers; and (2) relative deviation. This approach can also provide quantitative feedback in OPC errors which can be substantially useful for the end user. It is foreseen that the model can be transported across layers thereby reducing setup burden (e.g., since different models do not need to be generated for different specimen or process layers). The embodiments can also use a deep learning based classification model to learn post-OPC SEM contours when provided with pre-OPC design clips. A deep learning model can also be trained to extract contours from a SEM image. These two models advantageously enable fast, robust CD measurements for various applications. This method builds on and can be used with other deep learning applications such as deep learning based design contour rendering, deep learning based classification, and deep learning based single image detection.

The embodiments described herein propose a method that can either rely on receiving specific locations for characterizing pattern fidelity or more generally to characterize pattern fidelity for an area of interest like a static random access memory (SRAM) area, etc. The embodiments described herein advantageously overcome heuristic and parameter dependent contour generation and the challenges associated with complex patterns and pattern intersections. The embodiments described herein also advantageously address typical challenges observed during design rendering steps and edge extraction steps that are crucial to precision, robustness, and ease of use.

One embodiment of such a system is shown in FIG. 1. The system includes an imaging subsystem that includes at least an energy source and a detector. The energy source is configured to generate energy that is directed to a specimen. The detector is configured to detect energy from the specimen and to generate images responsive to the detected energy.

In one embodiment, the energy directed to the specimen includes light, and the energy detected from the specimen includes light. For example, in the embodiment of the system shown in FIG. 1, imaging subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the imaging subsystem may be configured to alter one or more characteristics of one or more elements of the illumination subsystem such that the light can be directed to the specimen at an angle of incidence that is different than that shown in FIG. 1. In one such example, the imaging subsystem may be configured to move light source 16, optical element 18, and lens 20 such that the light is directed to the specimen at a different angle of incidence.

In some instances, the imaging subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a tight source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e,g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for imaging.

The imaging subsystem may also include a scanning subsystem configured to cause the light to be scanned over the specimen. For example, the imaging subsystem may include stage 22 on which specimen 14 is disposed during imaging. The scanning subsystem may include any suitable mechanical and/or robotic assembly (that includes stage 22) that can be configured to move the specimen such that the light can be scanned over the specimen. In addition, or alternatively, the imaging subsystem may be configured such that one or more optical elements of the imaging subsystem perform some scanning of the light over the specimen. The light may be scanned over the specimen in any suitable fashion.

The imaging subsystem further includes one or more detection channels. At least one of the one or more detection channels includes a detector configured to detect light from the specimen due to illumination of the specimen by the imaging subsystem and to generate output responsive to the detected light. For example, the imaging subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the imaging subsystem that includes two detection channels, the imaging subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the imaging subsystem may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the images described herein in a number of ways.

It is noted that FIG. 1 is provided herein to generally illustrate a configuration of an imaging subsystem that may be included in the system embodiments described herein. Obviously, the imaging subsystem configuration described herein may be altered to optimize the performance of the system as is normally performed when designing a commercial imaging system. In addition, the systems described herein may be implemented using an existing imaging system (e.g., by adding functionality described herein to an existing imaging system) such as the SpectraShape family of tools and the Archer series of tools that are commercially available from KLA-Tencor. For some such systems, the methods described herein may be provided as optional functionality of the imaging system (e.g., in addition to other functionality of the system). Alternatively, the imaging subsystem described herein may be designed "from scratch" to provide a completely new system.

Computer subsystem 36 of the system may be coupled to the detectors of the imaging subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked toot.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the imaging subsystem is described above as being an optical or light-based imaging subsystem, the imaging subsystem may be an electron beam-based imaging subsystem. For example, in one embodiment, the energy directed to the specimen includes electrons, and the energy detected from the specimen includes electrons. In this manner, the energy source may be an electron beam source. In one such embodiment shown in FIG. 2, the imaging subsystem includes electron column which is coupled to computer subsystem(s) 124.

Figure 2:
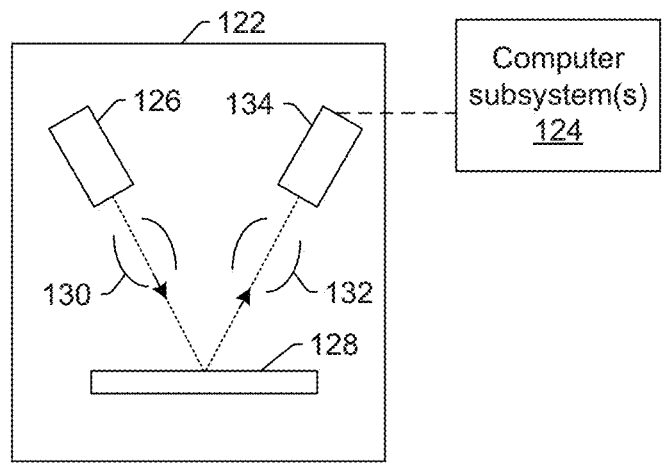

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based imaging subsystem may be configured to use multiple modes to generate images of the specimen (e.g., with different illumination angles, collection angles, etc.). The multiple modes of the electron beam-based imaging subsystem may be different in any image generation parameters of the imaging subsystem.

Computer subsystem(s) 124 may be coupled to detector 134 as described above. The detector may detect electrons returned from the surface of the specimen thereby forming electron beam images of the specimen. The electron beam images may include any suitable electron beam images. Computer subsystem(s) 124 may be configured to perform any of the functions described herein using the output of the detector and/or the electron beam images. Computer subsystem(s) 124 may be configured to perform any additional step(s) described herein. A system that includes the imaging subsystem shown in FIG. 2 may be further configured as described herein.

It is noted that FIG. 2 is provided herein to generally illustrate a configuration of an electron beam-based imaging subsystem that may be included in the embodiments described herein. As with the optical imaging subsystem described above, the electron beam-based imaging subsystem configuration described herein may be altered to optimize the performance of the imaging subsystem as is normally performed when designing a commercial system. In addition, the systems described herein may be implemented using an existing metrology or high resolution defect review system by adding functionality described herein to an existing system) such as the eDR-xxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the imaging subsystem is described above as being a light-based or electron beam-based imaging subsystem, the imaging subsystem may be an ion beam-based imaging subsystem. Such an imaging subsystem may be configured as shown in FIG. 2 except that the electron beam source may be replaced with any suitable ion beam source known in the art. In addition, the imaging subsystem may be any other suitable ion beam-based imaging subsystem such as those included in commercially available focused ion beam (FIB) systems, helium ion microscopy (HIM) systems, and secondary ion mass spectroscopy (SIMS) systems.

As noted above, the imaging subsystem is configured for scanning energy (e.g., light or electrons) over a physical version of the specimen thereby generating actual images for the physical version of the specimen. In this manner, the imaging subsystem may be configured as an "actual" tool, rather than a "virtual" tool. For example, a storage medium (not shown) and computer subsystem(s) 102 shown in FIG. 1 may be configured as a "virtual" tool. In particular, the storage medium and the computer subsystem(s) are not part of imaging subsystem 10 and do not have any capability for handling the physical version of the specimen. In other words, in tools configured as virtual tools, the output of its one or more "detectors" may be output that was previously generated by one or more detectors of an actual tool and that is stored in the virtual tool, and during the "scanning," the virtual tool may replay the stored output as though the specimen is being scanned. In this manner, scanning the specimen with a virtual tool may appear to be the same as though a physical specimen is being scanned with an actual tool, while, in reality, the "scanning" involves simply replaying output for the specimen in the same manner as the specimen may be scanned. Systems and methods configured as "virtual" inspection tools are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents. In addition, configuring the one or more virtual systems as a central compute and storage (CCS) system may be performed as described in the above-referenced patent to Duffy. The persistent storage mechanisms described herein can have distributed computing and storage such as the CCS architecture, but the embodiments described herein are not limited to that architecture.

As further noted above, the imaging subsystem may be configured to generate images of the specimen with multiple modes. In general, a "mode" can be defined by the values of parameters of the imaging subsystem used for generating images of a specimen or the output used to generate images of the specimen. Therefore, modes that are different may be different in the values for at least one of the imaging parameters of the imaging subsystem. For example, in one embodiment of an optical based imaging subsystem, at least one of the multiple modes uses at least one wavelength of light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the imaging subsystem that is different from an illumination channel of the imaging subsystem used for at least one other of the multiple modes. For example, as noted above, the imaging subsystem may include more than one illumination chancel As such, different illumination channels may be used for different modes.

In one embodiment, the system is configured as an inspection tool. For example, the optical and electron beam imaging subsystems described herein may be configured as inspection tools. In this manner, the image inputs to the deep learning model described herein are generated by an inspection tool in some embodiments. In another embodiment, the system is configured as a metrology tool. For example, the optical and electron beam imaging subsystems described herein may be configured as metrology tools. In a further embodiment, the system is configured as a defect review tool. For example, the optical and electron beam imaging subsystems described herein may be configured for defect review applications. In particular, the embodiments of the imaging subsystems described herein and shown in FIGS. 1 and 2 may be modified in one or more parameters to provide different imaging capability depending on the application for which they will be used. In one such example, the imaging subsystem shown in FIG. 1 may be configured to have a higher resolution if it is to be used for metrology rather than for inspection. In other words, the embodiments of the imaging subsystem shown in FIGS. 1 and 2 describe some general and various configurations for an imaging subsystem that can be tailored in a number of manners that will be obvious to one skilled in the art to produce imaging subsystems having different imaging capabilities that are more or less suitable for different applications.

The one or more computer subsystems are configured for acquiring the images of patterns formed on the specimen generated by an imaging subsystem described herein. Acquiring the images may be performed using one of the imaging subsystems described herein (e.g., by directing light or an electron beam to the specimen and detecting light or an electron beam, respectively, from the specimen). In this manner, acquiring the images may be performed using the physical specimen itself and some sort of imaging hardware. However, acquiring the images does not necessarily include imaging the specimen using imaging hardware. For example, another system and/or method may generate the images and may store the generated images in one or more storage media such as a virtual inspection system as described herein or another storage media described herein.

Therefore, acquiring the images may include acquiring the images from the storage media in which they have been stored.

The patterns formed on the specimen may include any patterns that can be formed on any specimen described herein (e.g., a reticle and wafer). For example, although some examples of images of patterns formed on a specimen are shown in figures described herein, those examples are not meant to be limiting examples or particular examples of any actual patterns. The patterns that are formed on the specimen may include different types of patterns such as lines, spaces, regular and irregular polygons, contacts, etc. In addition, the patterns that are formed on the specimen may be formed on different layer types (e.g., a metal layer, an interconnect layer, etc.). Furthermore, the patterns that are formed on the specimen may be formed in any suitable fabrication processes such as lithography processes, etch processes, chemical-mechanical polishing processes, etc. In other words, the embodiments described herein are not limited to any particular patterns for which the steps described herein can be performed.

The system also includes one or more components executed by the one or more computer subsystems. The component(s), e.g., component(s) 100 shown in FIG. 1, executed by the computer subsystem(s), e.g., computer subsystem 36 and/or computer subsystem(s) 102, include first learning based model 104 and second learning based model 106. The first learning based model is configured for generating simulated contours for the patterns based on a design for the specimen input to the first learning based model by the one or more computer subsystems, and the simulated contours are expected contours of a defect free version of the patterns in the images of the specimen generated by the imaging subsystem. The second learning based model is configured for generating actual contours for the patterns in at least one of the acquired images of the patterns formed on the specimen input to the second learning based model by the one or more computer subsystems. First and second learning models 104 and 106 may have one of the configurations described further herein and may be configured for generating the simulated and actual contours, respectively, as described herein.

The simulated contours are "expected contours" in that they are simulated for how the contours would be expected to appear in image(s) of a specimen generated by an imaging subsystem described herein if the patterns were formed on the specimen in a nominal or defect free manner. In other words, if the design that is input to the first learning based model was formed on the specimen without any defects formed therein and was then imaged by the imaging subsystem, the patterns in the images generated by the imaging subsystem would have the "expected contours." Therefore, the "simulated contours" approximate, simulate, or estimate how the contours would appear in images of a specimen on which the design is formed in a defect free manner. As such, generating the simulated contours would, if it were being done in a heuristic or deterministic manner, need to take into account both the formation of the patterned features on the specimen as well as the imaging of the specimen by the imaging subsystem.

Generating simulated contours for patterned features in a design as they would appear in an image of a specimen on which the design is formed is not a simple and easy task for a number of reasons. For example, due to the inherent limitations of the tools, materials, and processes used to form the structures on a specimen and then image the specimen, the structures will not necessarily be appear in images of the specimen as they are included in the design. In one such example, instead of patterns having sharp, 90 degree corners, the patterns will have at least somewhat rounded corners. In addition, any of the structures may have variations in dimensions such as width at various points across the structures. For example, the patterns may have some line width variations compared to the design characteristics of the patterns at multiple points across the patterns. Often, the effects of the fabrication process(es) and imaging process(es) on a design for patterned features is difficult to model due to the many variables involved and the ways in which those variables can drift from specimen-to-specimen and/or over time in addition to the other various possible noise sources that may affect the images generated for the patterns. The embodiments described herein, however, provide much simpler and/or more robust ways for generating simulated contours that can be used to generate much more precise estimations of the simulated contours.

"Actual contours" as that term is used herein is meant to be defined as the contours of patterned features as they appear in images of the specimen generated by an imaging subsystem. In this manner, unlike the "expected contours," the "actual contours" are contours generated for patterned features actually formed on a physical version of the specimen as those patterned features appear in actual images generated using the physical version of the specimen. The "actual contours" may therefore also be referred to herein as "extracted contours" in that the "actual contours" are extracted from actual images of the physical version of the specimen.

In one embodiment, the first and second learning based models are deep learning based models. In this manner, the embodiments described herein provide new features for semiconductor inspection, metrology, and other tools including deep learning based design contour rendering and deep learning based contour extraction from SEM and other images. Generally speaking, "deep learning" (also known as deep structured learning, hierarchical learning or deep machine learning) is a branch of machine learning based on a set of algorithms that attempt to model high level abstractions in data. In a simple case, there may be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Some representations are better than others at simplifying the learning task (e.g., face recognition or facial expression recognition). One of the promises of deep learning is replacing handcrafted features with efficient algorithms for unsupervised or semi-supervised feature learning and hierarchical feature extraction.

Research in this area attempts to make better representations and create models to learn these representations from large-scale unlabeled data. Some of the representations are inspired by advances in neuroscience and are loosely based on interpretation of information processing and communication patterns in a nervous system, such as neural coding which attempts to define a relationship between various stimuli and associated neuronal responses in the brain.

In another embodiment, the first and/or second learning based models are machine learning models. Machine learning can be generally defined as a type of artificial intelligence (AI) that provides computers with the ability to learn without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data—such algorithms overcome following strictly static program instructions by making data driven predictions or decisions, through building a model from sample inputs.

The machine learning described herein may be further performed as described in "Introduction to Statistical Machine Learning," by Sugiyama, Morgan Kaufmann, 2016, 534 pages; "Discriminative, Generative, and Imitative Learning," Jebara, MIT Thesis, 2002, 212 pages; and "Principles of Data Mining (Adaptive Computation and Machine Learning)," Hand et al., MIT Press, 2001, 578 pages; which are incorporated by reference as if fully set forth herein. The embodiments described herein may be further configured as described in these references.

In some embodiments, the first and/or second learning based models are configured as generative models. A "generative" model can be generally defined as a model that is probabilistic in nature. In other words, a "generative" model is not one that performs forward simulation or rule-based approaches. Instead, as described further herein, the generative model can be learned (in that its parameters can be learned) based on a suitable training set of data. In one embodiment, the first and/or second learning based models are configured as deep generative models. For example, the models may be configured to have a deep learning architecture in that the models may include multiple layers, which perform a number of algorithms or transformations.

In another embodiment, the first and/or second learning based models are configured as neural networks. In a further embodiment, the first and/or second learning based models are configured as deep neural networks, each with a set of weights that model the world according to the data that it has been fed to train it. Neural networks can be generally defined as a computational approach which is based on a relatively large collection of neural units loosely modeling the way a biological brain solves problems with relatively large clusters of biological neurons connected by axons. Each neural unit is connected with many others, and links can be enforcing or inhibitory in their effect on the activation state of connected neural units. These systems are self-learning and trained rather than explicitly programmed and excel in areas where the solution or feature detection is difficult to express in a traditional computer program.

Neural networks typically consist of multiple layers, and the signal path traverses from front to back. The goal of the neural network is to solve problems in the same way that the human brain would, although several neural networks are much more abstract. Modern neural network projects typically work with a few thousand to a few million neural units and millions of connections. The neural network may have any suitable architecture and/or configuration known in the art.

In one embodiment, the first and/or second learning based models are configured as AlexNets. For example, an AlexNet includes a number of convolutional layers (e.g., 5) followed by a number of fully connected layers (e.g., 3) that are, in combination, configured and trained to classify images. Examples of neural networks configured as AlexNets are described in "ImageNet Classification with Deep Convolutional Neural Networks" by Krizhevsky et al., NIPS 2012, which is incorporated by reference as if fully set forth herein. The models described herein may be further configured as described in this reference.

In another such embodiment, the first and/or second learning based models are configured as GoogleNets. For example, a GoogleNet may include layers such as convolutional, pooling, and fully connected layers such as those described further herein configured and trained to classify images. While the GoogleNet architecture may include a relatively high number of layers (especially compared to some other neural networks described herein), some of the layers may be operating in parallel, and groups of layers that function in parallel with each other are generally referred to as inception modules. Other of the layers may operate sequentially. Therefore, GoogleNets are different from other neural networks described herein in that not all of the layers are arranged in a sequential structure. Examples of neural networks configured as GoogleNets are described in "Going Deeper with Convolutions," by Szegedy et al., CVPR 2015, which is incorporated by reference as if fully set forth herein. The models described herein may be further configured as described in this reference.

In a further such embodiment, the second learning based model has a VGG network architecture. For example, VGG networks were created by increasing the number of convolutional layers while fixing other parameters of the architecture. Adding convolutional layers to increase depth is made possible by using substantially small convolutional filters in all of the layers. Like some other neural networks described herein, VGG networks were created and trained to classify images. VGG networks also include convolutional layers followed by fully connected layers. Examples of neural networks configured as VGG are described in "Very Deep Convolutional Networks for Large-Scale Image Recognition," by Simonyan et al., ICLR 2015, which is incorporated by reference as if fully set forth herein. The models described herein may be further configured as described in this reference.

In another embodiment, the second learning based model is configured as a holistically-nested edge detection model. Edge extraction is a vital step that determines the precision and robustness of CD measurements. This step may be performed after the setup of parameters that may be tweaked for robustness and noise handling. The currently used approaches also struggle to handle complex and crossing patterns. In the embodiments described herein, a deep learning based approach named holistically-nested edge detection can be used to predict contours provided a specimen image. This deep learning approach is scalable to new layers, and the user merely would need a few example images to "teach" the model what is a contour on a new layer.

In this manner, deep learning based SEM image contour generation may be performed using holistically-nested edge detection (HED) algorithm(s) to extract contours from SEM images. Using such algorithm(s) is expected to overcome the Challenges with the currently used contour algorithms. In such algorithm(s), side-output layers are inserted after convolutional layers. Deep supervision is imposed at each side-output layer, guiding the side-outputs towards edge predictions with the characteristics that are desired. The outputs of HED are multi-scale and multi-level, with the side-output-plane size becoming smaller and the receptive field size becoming larger. One weighted-fusion layer is added to automatically learn how to combine outputs from multiple scales. The entire network may be trained with multiple error propagation paths. The HED algorithm(s) have shown state of the art edge extraction performance on the BSDS500 dataset, which is available in the art. It also demonstrated excellent edge extraction performance on SEM data. The holistically nested edge detection models described herein may be further configured as described by Xie et al., in "Holistically Nested Edge Detection," arXiv: 1504.06375v2, 4 Oct. 2015, 10 pages, which is incorporated by reference as if fully set forth herein. The embodiments described herein may be further configured as described in this publication. In addition, the second learning based model may be configured for multi-scale edge detection using the first 5 stages of a VGG network architecture, which may be configured as described further herein, (strides of 1, 2, 4, 8, and 16) with single fused output.

In some such embodiments, the first and/or second learning based models are configured as deep residual networks. For example, like some other networks described herein, a deep residual network may include convolutional layers followed by fully connected layers, which are, in combination, configured and trained for image classification. In a deep residual network, the layers are configured to learn residual functions with reference to the layer inputs, instead of learning unreferenced functions. In particular, instead of hoping each few stacked layers directly fit a desired underlying mapping, these layers are explicitly allowed to fit a residual mapping, which is realized by feedforward neural networks with shortcut connections. Shortcut connections are connections that skip one or more layers. A deep residual net may be created by taking a plain neural network structure that includes convolutional layers and inserting shortcut connections which thereby takes the plain neural network and turns it into its residual learning counterpart. Examples of deep residual nets are described in "Deep Residual Learning for Image Recognition" by He et al., NIPS 2015, which is incorporated by reference as if fully set forth herein. The deep learning models described herein may be further configured as described in this reference.

In a further such embodiment, the first and/or second learning based models include one or more fully connected layers. A "fully connected layer" may be generally defined as a layer in which each of the nodes is connected to each of the nodes in the previous layer. The fully connected layer(s) may perform classification based on the features extracted by convolutional layer(s), which may be configured as described further herein. The fully connected layer(s) are configured for feature selection and classification. In other words, the fully connected layer(s) select features from a feature map and then classify properties in the image(s) based on the selected features. The selected features may include all of the features in the feature map (if appropriate) or only some of the features in the feature map.

In some embodiments, the information determined by the first and/or second learning based models includes features of the images extracted by the first and/or second learning based models. In one such embodiment, the first and/or second learning based models include one or more convolutional layers. The convolutional layer(s) may have any suitable configuration known in the art and are generally configured to determine features for an image as a function of position across the image (i.e., a feature map) by applying a convolution function to the input image using one or more filters. In one embodiment, the first learning based model (or at least a part of the first learning based model) is configured as a convolution neural network (CNN). For example, the first learning based model may be configured as a CNN, which is usually stacks of convolution and pooling layers, to extract local features. The embodiments described herein can take advantage of deep learning concepts such as a CNN to solve the normally intractable representation inversion problem. The first learning based model may have any CNN configuration or architecture known in the art. The one or more pooling layers may also have any suitable configuration known in the art (e.g., max pooling layers) and are generally configured for reducing the dimensionality of the feature map generated by the one or more convolutional layers while retaining the most important features.

In a further embodiment, the first learning based model is configured as a deep generative model using variational auto-encoders. For example, the embodiments described herein may use a deep generative model using variational auto-encoders (VAE) instead of other design rendering approaches that are discriminative approaches. Such a first learning based model allows adding uncertainties along with the design contour generation, which in turn will further improve robustness to false positives. A variational auto-encoder is a component that takes the merits of deep learning and variational inference and leads to significant advances in generative modeling. In addition or alternatively, a variational autoencoder (VAE) combined with a generative adversarial network (GAN) or a deep generative adversarial network (DGAN)) may be configured as described in "Adversarial Autoencoders," Makhzani et al., arXiv: 1511.05644v2, May 25, 2016, 16 pages, which is incorporated by reference as if fully set forth herein. The embodiments described herein may be further configured as described in this reference.

The features determined by the first and/or second learning based models may include any suitable features described further herein or known in the art that can be inferred from the input described herein (and possibly used to generate other output described further herein). For example, the features may include a vector of intensity values per pixel. The features may also include any other types of features described herein, e.g., vectors of scalar values, vectors of independent distributions, joint distributions, or any other suitable feature types known in the art.

The first and second learning based models may be further configured as described in U.S. Patent Application Publication Nos. 2017/0148226 published May 25, 2017 by Zhang et al., 2017/0193680 published Jul. 6, 2017 by Zhang et al., 2017/0194126 published Jul. 6, 2017 by Bhaskar et al., 2017/0200260 published Jul. 13, 2017 by Bhaskar et al., 2017/0200265 published Jul. 13, 2017 by Bhaskar et al., 2017/0345140 published Nov. 30, 2017 by Zhang et. al., and U.S. patent application Ser. No. 15/694,719 filed Sep. 1, 2017 by Zhang et al. and U.S. Ser. No. 15/697,426 filed Sep. 6, 2017 by lie et al., which are incorporated by reference as if fully set forth herein. The embodiments described herein may be further configured as described in these publications and patent applications.

In one embodiment, the design input to the first learning based model does not include features of the design that will not be printed on the specimen. In other words, the features of the design input to the first learning based model may be pre-OPC features and/or the design that does not include any OPC features of the design that affect how features are printed on the specimen but in of themselves are not printed on the specimen. Accurately rendering pre-OPC design to SEM-like contours can be performed with complex simulations but requires lots of computing and needs to get the parameters right. Instead, if the design to SEM rendering is performed with a learning based regression model such as one of those described further herein that learns how to render design contours from pre-OPC design clips, the results are excellent and can be done at a relatively low cost of initial training setup. The rendering then provides reference contours for use in identifying outliers of pattern fidelity, which may be performed as described further herein.

In one embodiment, the first and second learning based models are adaptable to different pattern types. In another embodiment, the first and second learning based models are adaptable to different pattern densities. In an additional embodiment, the first and second learning based models are adaptable to patterns in different layer types. In a further embodiment, the first and second learning based models are adaptable to images generated by the imaging subsystem with one or more different imaging parameters. For example, the models described herein are robust and generalized to various pattern types, pattern density, layer types memory or logic) and image modalities (optical, SEM, x-ray, etc.).

Different pattern types may include patterns that have different polygonal shapes, patterns that correspond to different features of the devices being formed on the specimen, etc. Different pattern densities may include relatively sparse features and relatively dense features and may be defined quantitatively by the calculated density of the features in a given area. Different layer types may include different layer types on the same specimen (e.g., different layers being formed one on top of each other on a wafer) and/or different layer types formed on different specimens (e.g., where devices are fabricated on one specimen with first layer types and on another specimen with second layer types). The one or more different imaging parameters may include any of the imaging parameters described herein that collectively define an imaging mode of an imaging subsystem. In addition, as described above, the models are adaptable to different image modalities. Therefore, the one or more different imaging parameters may include optical imaging parameters and electron beam (or other non-optical) imaging parameters.

In one such example, the design contours can be rendered substantially accurately by the learning based models described herein after learning the lithography/etch process, which can then be compared to image contours in order to flag potential OPC errors as described further herein. The first learning based model can be trained when a relatively large number of images of nominal patterns (i.e., patterns without OPC errors) are available to train the first learning based model such that it thereby "teams" the lithography/etch process and the imaging process. For new layers, new examples can be added to the training set used for training the first learning based model, and either retraining from scratch or fine tuning of the first learning based model using the initial weights and/or other parameters from the existing model can be performed. Fine tuning means that the initial values of the model parameters are loaded from a pre-existing trained model, and the model parameters are retrained using the new training images. Fine tuning typically advantageously requires fewer images than training from scratch. Similar steps may be performed to train the first learning based model for different pattern types, pattern densities, imaging parameter(s), etc. The second learning based model can be adaptable to such variations in a similar manner. The first and second learning based models may be trained as described further herein.

Figure 3:
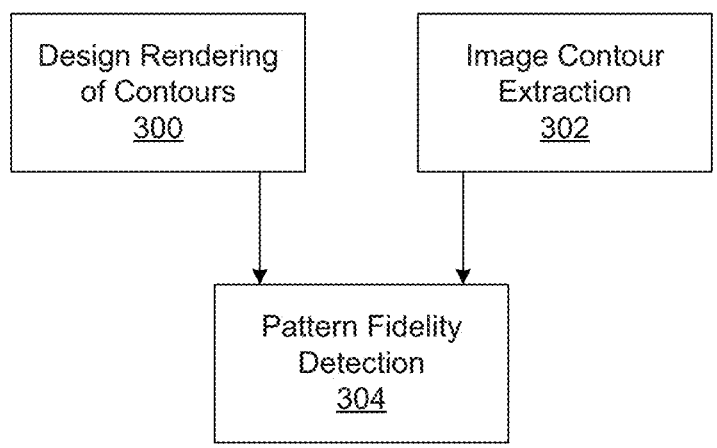
FIGS. 3-5 and 7 are flow charts illustrating embodiments of steps that may be performed by various embodiments described herein.

The one or more computer subsystems are further configured for comparing the actual contours to the simulated contours and detecting defects in the patterns formed on the specimen based on results of the comparing. For example, as shown in FIG. 3, the one or more computer subsystems may be configured for design rendering of contours, as shown in step 300, which may be performed as described further herein. In addition, as shown in FIG. 3, the one or more computer subsystems may be configured for image contour extraction, as shown in step 302, which may be performed as described further herein. Furthermore, as shown in FIG. 3, the computer subsystem(s)) may be configured for comparing the contours determined from the rendered design to the contours extracted from the image for pattern fidelity detection in step 304.

Comparing the actual contours to the simulated contours may include aligning the actual contours to the simulated contours. For example, one or more features of the design that are included in both the rendered design and the images may be identified as suitable for alignment (e.g., based on their uniqueness relative to other nearby/surrounding patterns and based on their characteristics that make them suitable for alignment in x and/or y). The rendered design and the images may then be aligned using the feature(s) as they appear in the rendered design and the images. The spatial relationships between: (1) the aligned rendered design and the images; (2) the contours determined for the rendered design and the rendered design; and (3) the contours extracted from the images and the images themselves may then be used to align the contours determined from the rendered design to the contours extracted from the images. The alignment may be performed for every image frame or job whose contours will be compared to the simulated contours or it may be performed for fewer than all of the image frames or jobs (e.g., when the alignment results such as an alignment offset determined for one image frame or job can be used to align other image frames or jobs). Aligning the rendered design and the images may be further performed as described in the patent issued to Kulkarni et al. that is incorporated by reference as if fully set forth herein. The embodiments described herein may be further configured as described in this patent.

Once the contours are aligned, they can be compared. In one embodiment, the results of the comparing include quantitative differences between dimensions of a first of the patterns in the design and the first of the patterns in the at least one of the acquired images of the patterns formed on the specimen determined based on differences between the actual and simulated contours, and detecting the defects includes applying a threshold to the quantitative differences between the dimensions. In one such instance, the comparisons include comparing the locations of the contours on a pixel-by-pixel basis and determining differences in the locations of the contours. Those differences can then be used to determine quantitative differences between the dimensions of the patterns. Detecting the defects may then include applying a threshold to the quantitative differences. Patterns having a difference above the threshold may be identified as defects while patterns not having a difference above the threshold may not be identified as defects. In this manner, the defects that are detected by the computer subsystem(s) may be pattern fidelity defects i.e., defects in the patterned features themselves as opposed to other defects such as foreign particulates and contamination, scratches and other marks, etc.).

In another embodiment, the results of the comparing include quantitative differences between the actual and simulated contours for each of the pixels of each of the patterns in the at least one of the acquired images. For example, semiconductor manufacturing typically requires a relatively high fidelity pattern characterization measurement relative to intended design. The embodiments described herein are able to perform relatively large area measurements in a single shot (much like a detection algorithm) except that it returns quantitative measurements for each pixel. The quantitative differences between the actual and simulated contours may be determined for each of the pixels as described further herein. Furthermore, because the embodiments described herein can determine differences between contours for each pixel in each of the patterns, the embodiments can be used to automatically flag potential defective (pattern defects only) locations within the entire field of view that can be used as target areas for CD measurements (thereby eliminating any need for predetermined regions of interest in which measurements are made).

The embodiments described herein may also be configured for determining critical dimension uniformity (CDU) for individual features, for some portion of the features, for multiple instances of the same type of feature, etc. The CDU may be determined in any suitable manner known in the art. In addition, the embodiments described herein may be used for logic CDU use cases. For example, logic CDU use cases sometimes includes steps such as measurements at known hot spots, area inspection—pattern fidelity measurements, and defect detection and measurements. In this manner, the embodiments described herein can be used in the area inspection—pattern fidelity measurements step.

In this manner, the embodiments described herein provide new features for semiconductor inspection, metrology, and other tools including a contour-based defect detection method and system. The contour-based pattern fidelity detection is different from other comparisons performed in other methods for pattern fidelity detection. For example, in rendered image to target image comparisons, an image rendered from design may be compared to an image generated from a physical specimen, and results of the comparison may be used for pattern fidelity detection. In another example, in design-to-database type comparisons, a design clip and an image of the portion of the design corresponding to the design clip formed on a physical specimen can be compared, and results of the comparison can be used for pattern fidelity detection.

In contrast, in contour-based pattern fidelity detection, contours determined from design rendering and contours extracted from images generated for a physical specimen are compared, and results of the comparisons can be used for pattern fidelity detection. Therefore, unlike the other methods described above, the contour-based approach does not involve comparing a simulated image to an actual image and/or comparing a design clip to an actual image. Instead, the embodiments described herein involve comparing contours determined from design rendering to contours determined from images of a specimen to thereby detect defects in patterns formed on the specimen. Furthermore, comparing a simulated image to an actual image and comparing a portion of a design to an actual image involve comparing the images to each other or the design to the image, which is different from the comparisons described herein in which characteristics (i.e., contours of the patterns in the images) are compared to each other. In other words, in the comparisons described herein, the images themselves are not compared to each other or to a design. Instead, characteristics of the patterned features derived from the images and design are compared to each other. The contour-based approach provides a quantitative metric for pattern fidelity detection. In addition, as described further herein, the contour based approach can be used to identify hot spots in the design.

The embodiments described herein also provide single die measurement solutions with the following benefits. For example, the embodiments described herein can detect hard repeaters (i.e., repeaters that occur in every die on a specimen) since the design rendered contours and therefore the design is used as the reference. In addition, the embodiments described herein provide throughput benefits as compared to the die-to-die approach used for extracting reference contours. Furthermore, the embodiments described herein do not require a reference die for reference contours. In particular, with a reference die approach, it can be hard to find a good nominal reference die on some highly defective wafers or some process window qualification (PWQ) wafers with zero process window.

In some embodiments, the one or more computer subsystems are configured for detecting hot spots in the design based on the detected defects. For example, the embodiments described herein are capable of identifying "hot spots" where the printed pattern is significantly different from the intended design. In particular, the embodiments described herein can compare SEM and design contours determined using learning based models for hot spot pattern quantification. The embodiments described herein allow for a generalized hot spot discovery method that goes beyond the standard lithography hot spots.

"Hot spots" can be generally defined as locations in a design that when printed on a specimen are more prone to defects than other locations in the design. For example, as the parameters of a fabrication process used to form patterned features on a specimen drift farther away from nominal (i.e., towards the edges of the process window), defects may appear at locations of "hot spots" on the specimen before other locations on the specimen. Therefore, it may be advantageous to identify hot spots in a design so that the corresponding locations on a specimen are monitored more closely for defects, which can enable early detection of a process problem. In some instances, it may be advantageous to identify hot spots as any location of any defect detected in patterned features formed on a specimen e.g., depending on the threshold used for detecting the defects and/or the process parameters that were used to print the design on the specimen). The hot spots can then be modified as more and more specimens are inspected (e.g., hot spots can be deleted When the hot spots do not consistently exhibit defects and added when new hot spots are discovered). In addition, since the hot spots can be identified as described herein by comparing contours extracted from specimen images to contours rendered from design, the contour comparisons described herein will not be subject to the disadvantages of die-to-die methods in which hard repeaters (defects that repeat at each of the same within die locations, each of the same within reticle locations, etc.) cannot be detected because the hard repeaters occur in both instances that are being compared to each other. Hot spots can also be identified by applying some threshold to the defects (e.g., defects that are bigger than some threshold are identified as the hot spots).

In one embodiment, the one or more computer subsystems are configured for training the first learning based model using a training data set that includes different portions of at least one training design for at least one training specimen and corresponding contour information extracted from training images of the at least one training specimen with a ground truth method. For example, during training, images of a specimen (e.g., SEM images) can be annotated (e.g., by a user or a ground truth method) with contours of the features in the images. The annotation may generate a binary ground truth image. The contour ground truth can come from the user or using existing edge extraction algorithms or a combination of both. Annotation is the marking of the ground truth manually or doing touch ups on the edges extracted using existing edge extraction algorithms. Those annotated images and/or the ground truth contour information for the features in the images can be used with corresponding design information for the features for design rendering training in which a design rendering model (i.e., the first learning based model) is trained.

The training data set may include any suitable number of portions of the at least one training design. The at least one training design may include multiple similar designs (e.g., designs for the same layers and same device types) or multiple different designs (e.g., any type of designs). The at least one training design may also include the design for the specimens that will be inspected using the simulated contours generated by the first learning based model. The at least one training specimen may be a specimen having the same layer type as the specimen that will be inspected although other specimen types may also be used as the training specimen(s). The training images may be acquired using any of the imaging subsystem(s) described herein and will generally include actual images generated by imaging subsystem(s) for physical version(s) of the training specimen(s).

Figure 4:
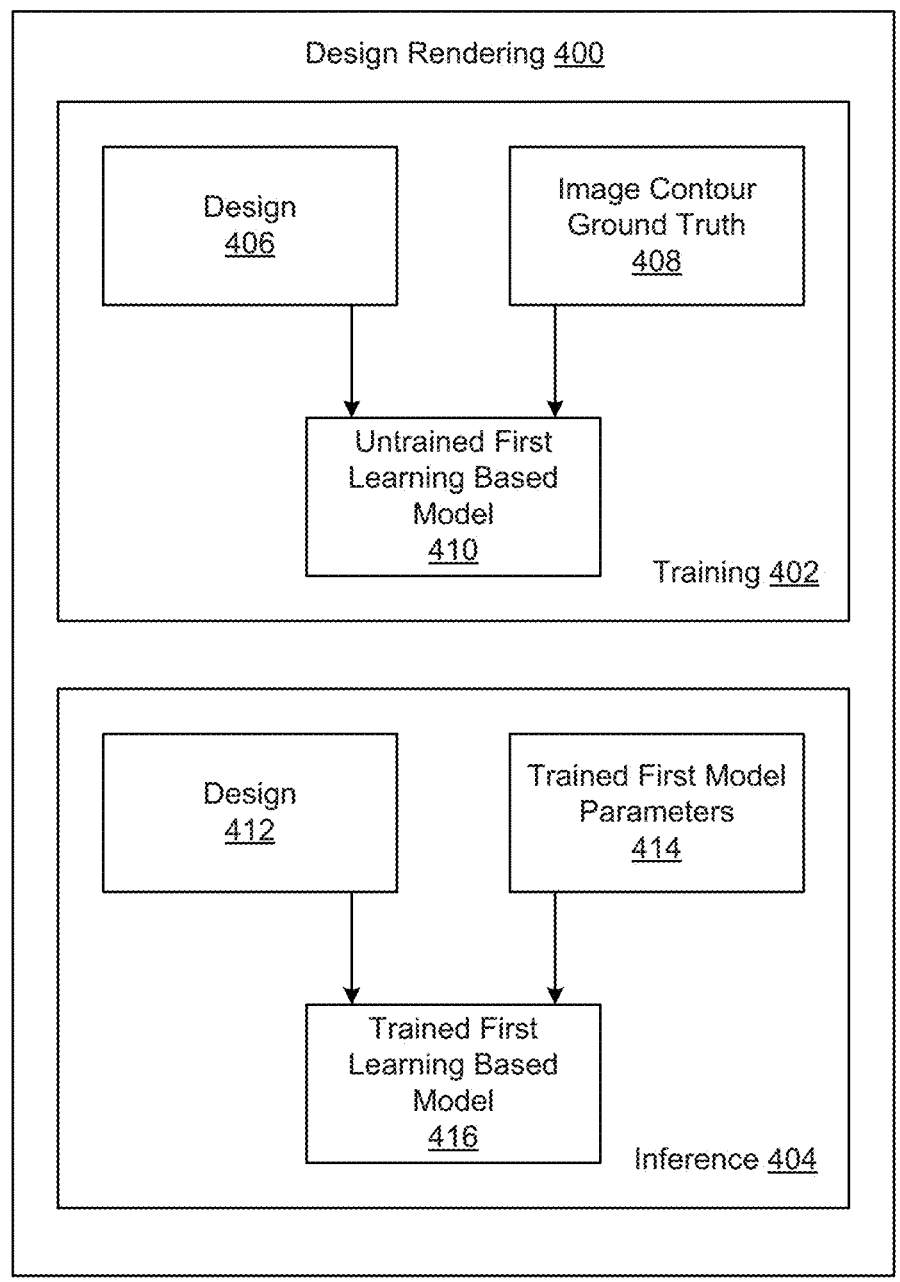

In one such example, as shown in FIG. 4, design rendering 400 may include two different phases: training 402 and inference 404. During training 402, design 406 and image contour ground truth 408 may be input to untrained first learning based model 410. One or more parameters of the untrained first learning based model may be altered until the simulated contours that are generated for design 406 by the untrained first learning based model match image contour ground truth 408 (where "match" means that an exact match has been found or the best possible "match" is identified once some stopping criteria has been reached). In other words, design 406 may be input to untrained first learning based model 410. The untrained first learning based model may then generate simulated contours for the design. The simulated contours can be compared to image contour ground truth 408 and if there are differences between the simulated contours and image contour ground truth 408, then one or more parameters of the model may be altered and the steps described above may be repeated until the simulated contours match the image contour ground truth. Then, during inference phase 404 of design rendering 400, design 412 is input to trained first learning based model 416 along with trained first model parameters 414, which were determined during the training phase. The trained first learning based model is trained as described above. The trained parameters may be input with the design such that the trained model generates simulated contours for design 412 with trained parameters 414. The simulated contours generated by the trained model may be used for pattern fidelity detection as described further herein.

In another example of training the design contour rendering model (i.e., the first learning based model), the first step may be to prepare the ground truth for training. Preparing the ground truth for training may include running an edge detection algorithm (e.g., canny detector) on images of nominal patterns (i.e., defect free patterns, patterns formed with nominal process parameters, etc.) to provide ground truth contour information. For example, a specimen image such as a SEM image can be input to a SEM contours extraction step to thereby generate ground truth SEM contours. The ground truth SEM contours can be input to a pattern/background labels creation step to thereby generate ground truth labels. The pre-OPC design may be rendered to a trivially rendered image and provided as an input to the untrained first learning based model. For example, for training, a design clip can be input to a "render design image" step to thereby generate a computer-aided design (CAD) image. The output of the edge detector is used as the target image.

The specimen image and design clip are then aligned to each other to ensure that the input and output data are in the same coordinate system. For example, a SEM image and a CAD image can be input to a CAD to SEM registration step to thereby produce an aligned CAD image. A simple CNN may then be used to train this model. For example, the CNN may include a number of convolution layers (e.g., two or more convolution layers) followed by a number of fully connected layers (e.g., two or more fully connected layers). The CNN may generate output that has pattern and background scores to differentiate between areas of the images that are patterns versus areas of the images that are background. For simplicity, the input images may be downsampled by half. The aligned CAD image and the ground truth labels can be input to a training step to thereby generate the trained first learning based model.

In another embodiment, the one or more computer subsystems are configured for training the second learning based model using a training data set that includes different training images generated by the imaging subsystem for at least one training specimen on which at least one training design was formed and corresponding contour information extracted from the different training images with a ground truth method. For example, during training, images of a specimen (e.g., SEM images) can be annotated (e.g., by a user or a ground truth method) with contours of the features in the images. The annotation may generate a binary ground truth image. Those annotated images and/or the ground truth contour information for the features in the images can be used with the images for image contour extraction training in which an image contour extraction model is trained. In addition, the binary ground truth image (or other ground truth contour information described herein) can be used to train a learning based model for both contour extraction and design rendering and output model parameters after training.

This training data set may include any suitable number of different training images. The different training images may be generated from a single specimen or multiple training specimens on which multiple similar designs (e.g., designs for the same layers and same device types) or multiple different designs (e.g., any type of designs) are formed. The at least one training design and the at least one training specimen may be configured as described further above. The different training images may be acquired using any of the imaging subsystem(s) described herein and will generally include actual images generated by imaging subsystem(s) for physical version(s) of the training specimen(s).

Figure 5:
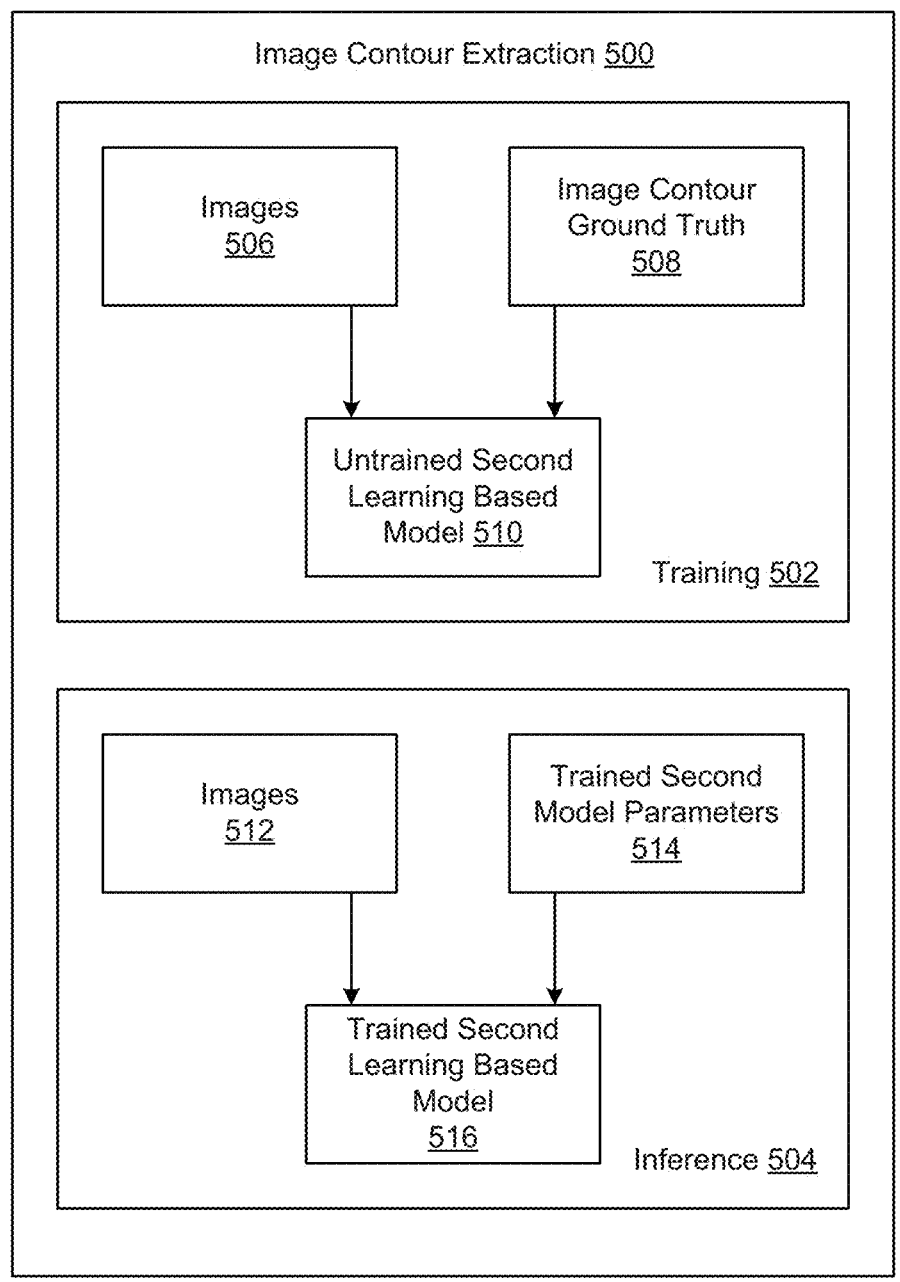

In one such example, as shown in FIG. 5, image contour extraction 500 may include two different phases: training 502 and inference 504. During training 502, images 506 and image contour ground truth 508 are input to untrained second learning based model 510. The image contour ground truth may be acquired in any suitable manner. For example, a user of the methods and systems may annotate the images with the image contour ground truth, which may include drawing the contours on the images. In this manner, one or more parameters of the untrained second learning based model may be altered until the contours that are generated for images 506 match image contour ground truth 508 (where "match" is defined in the same manner as described above). In other words, images 506 may be input to untrained second learning based model 510. The untrained second learning based model may then generate extracted contours for the images. The extracted contours can be compared to image contour ground truth 508 and if there are differences between the extracted contours and image contour ground truth 508, then one or more parameters of the model may be altered and the steps described above may be repeated until the extracted contours "match" the image contour ground truth.

During inference phase 504 of image contour extraction 500, images 512 may be input to trained second learning based model 516 along with trained second model parameters 514. The trained second learning based model is trained as described above. The trained parameters may be input with the images such that the trained model generates extracted contours for images 512 with trained parameters 514. The extracted contours generated by the trained model may be used for pattern fidelity detection as described further herein. In addition, the deep learning based image extracted contours can be used as seed points for substantially precise edge localization (within a relatively small neighborhood) in order to extract sub-pixel contour/edge locations (which could be important for some measurement use cases where precision requirements are substantially tight, i.e., where 1 pixel error could be quite large).

Figure 6:
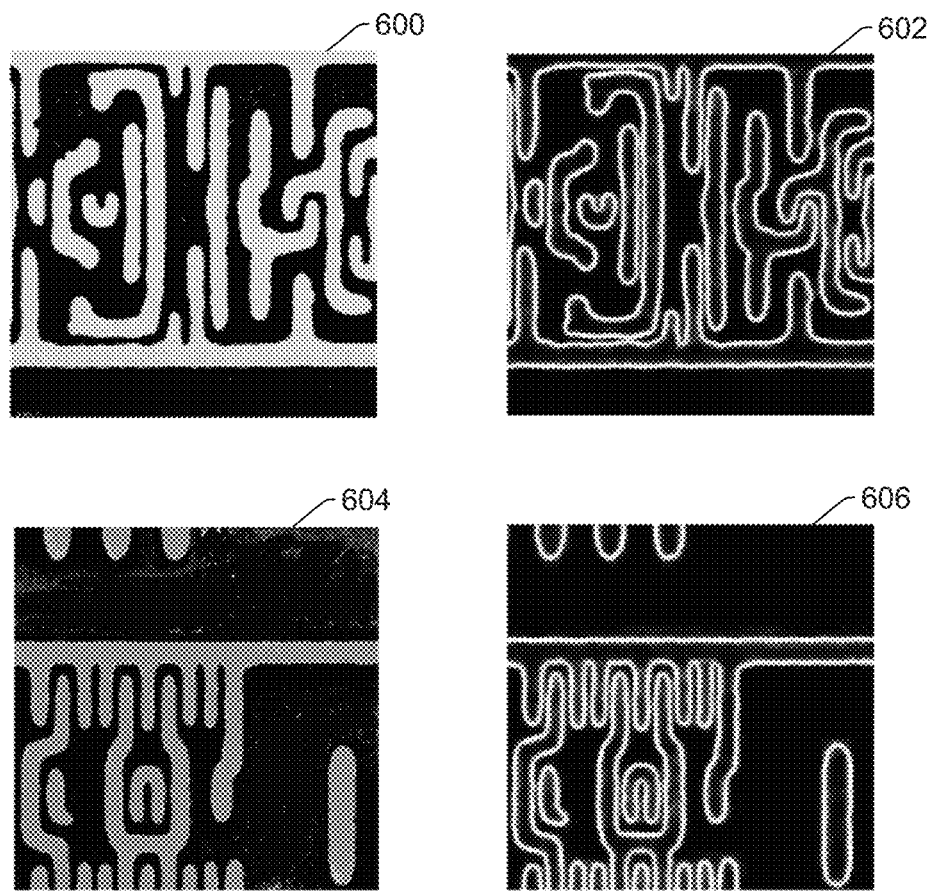
FIG. 6 is a schematic diagram illustrating images generated for a specimen on which patterns are formed and contours that are extracted by the embodiments described herein for the images.

FIG. 6 illustrates examples of images that may be input to the second learning based model described herein and extracted contours that may be generated for these images. For example, image 600 is in this example a SEM image generated for a semiconductor wafer. The image may be input to a trained second learning based model with the trained parameters as described herein, and the trained second learning based model may output extracted contours 602. In addition, image 604, which is also in this example a SEM image generated for a semiconductor wafer, may be input to a trained second learning based model with the trained parameters as described herein. The trained second learning based model may then output extracted contours 606. The images shown in FIG. 6 are not included herein to show any particular image types and/or any particular design or features formed on any particular specimen. Instead, these images and the contours extracted therefrom are included here to illustrate the capability of the second learning based model for extracting substantially precise contours for various patterned features shown in the images. In addition, although extracted contours 602 and 604 are shown in FIG. 6 as binary images, the extracted contours (as well as the design rendered contours) may be expressed in any other suitable manner.

Figure 7:
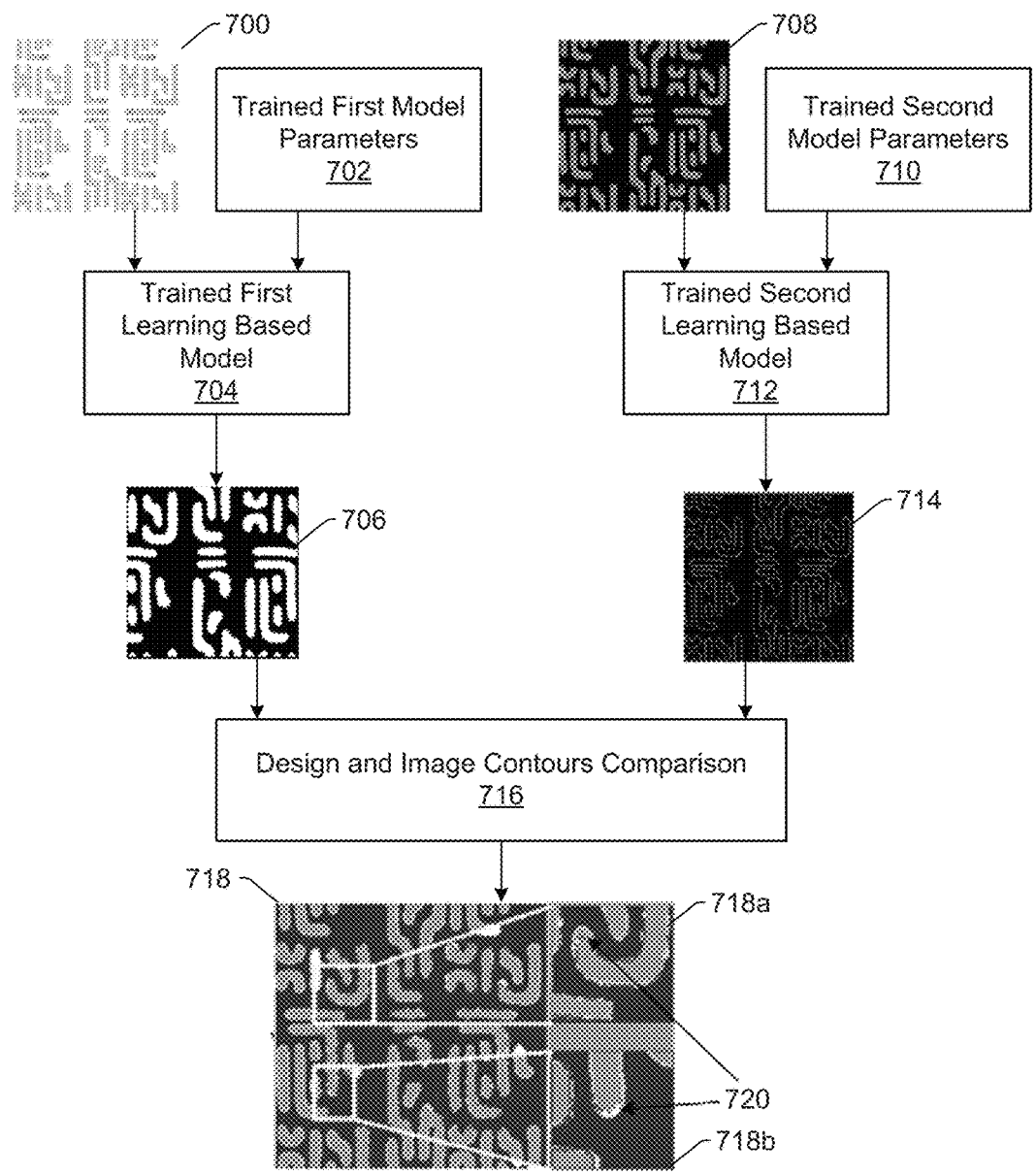

After both the design rendering model and the image contour extraction model (i.e., the first and second learning based models) are trained, the models can be used for runtime inference as described further herein. One such embodiment of contour based outlier detection algorithm runtime flow is shown in FIG. 7. For example, a design can be input to the design rendering model for deep learning based design contour rendering thereby generating rendered design contours. In particular, as shown in FIG. 7, design 700 and trained first model parameters 702 may be input to trained first learning based model 704 to thereby generate simulated contours 706. The first learning based model may include any of the design rendering networks described herein and the simulated contours may serve as the rendered nominal design contours for additional steps described herein.

In one such example, during runtime, the model may be provided with a trivially rendered pre-OPC design clip to obtain a "heat map" with scores corresponding to prediction of the existence of patterns. The "heat map" may then be thresholded to obtain the contours. More specifically, the first learning based model can be applied to a test design clip to obtain a scores map. The scores map can then be thresholded using a threshold such as 0.5 to thereby generate pattern and background predictions. The pattern and background predictions can then be used to extract boundaries to thereby generate predicted contours. The predicted contours may then be input to one or more post-processing steps to thereby generate the predicted contours.

Results produced by design contour rendering described herein demonstrated that the embodiments described herein are capable of advantageously generating design contours with substantially high precision. For example, the precision of predicted contour rendering from pre-OPC design was measured by comparing it to edges extracted from corresponding SEM images. More than 90% of the pixels were found to be within an error of 1.5 pixels.

In addition, an image of a specimen a SEM image) can be input to the image contour extraction model for deep learning based contour extraction to thereby generate image contours. For example, as shown in FIG. 7, image 708, which in this instance is shown as a SEM image, and trained second model parameters 710 are input to trained second learning based model 712 to thereby generate extracted contours 714. The trained second learning based model may include any of the image contour extraction networks described herein. Results of performing the edge extraction as described herein demonstrated excellent edge extraction performance on SEM data.

The rendered design contours and the image contours can be compared in an image and design contours comparison step, which may be performed to detect potential hot spots in the design. For example, as shown in FIG. 7, rendered contours 706 and extracted contours 714 may be input to design and image contours comparison step 716 in which the contours rendered from the design are compared to the contours extracted from the image. One or more measurement algorithms may then he used to perform CD measurements at the locations of the potential hot spots. For example, the design contouring rendering module and the SEM contour extraction module can be combined to compare the predicted contour to the extracted contour to measure CDs all over the image.

In some instances, the simulated contours may be compared to the extracted contours by overlaying the simulated contours with the extracted contours as shown by overlay 718. The simulated contours and extracted contours can be overlaid as described herein (e.g., via the alignment steps described herein). The overlay of the simulated and extracted contours may be used to perform measurements of the differences between the contours. For example, as shown by portion 718a of the overlay, portions of the simulated and extracted contours are spaced from one another in this portion. In addition, as shown by portion 718b of the overlay, portions of other simulated and extracted contours are spaced from one another. The portions of the simulated and extracted contours that are different from each other are shown by reference numeral 720.

In some instances, portions 718a and 718b can be identified by comparing non-overlapping contours (i.e., pattern deviations) to a user-defined threshold and flagging any deviations that exceed the user-defined threshold. In this manner, significant non-nominal pattern deviations can be identified and then measured. Measurements can be performed at the locations of these non-overlapping portions of the simulated and extracted contours by determining the number of pixels between the spaced apart, non-overlapping portions of the contours. Based on the pixel size in the images (determined from the parameters of the imaging subsystem used to generate the images), the distance between the non-overlapping contours can be determined thereby providing a measure or measurement of the distance between the two contours.

In the contour comparison results, different Euclidean distances between expected and extracted contours can be marked in different colors. For example, expected and extracted contours that are different by more than 3 pixels can be marked in one color, expected and extracted contours that are different by more than 2 pixels can be marked in a different color. Each of these steps may be performed as described further herein.

The embodiments described above have, therefore, a number of advantages. For example, the embodiments described above have demonstrated capability for robustly and generally allowing pattern fidelity to he characterized. The thresholding of the Euclidean distance allows for flexibility to monitor at different levels. Perhaps at early research and development phases, this thresholding can be loose and can be tightened during the high value production phase.

In some embodiments, the one or more computer subsystems are configured for performing an additional comparing step in which the actual contours for the same patterns formed in different dies on the specimen are compared to each other and detecting defects in the same patterns based on results of the additional comparing step. For example, one advantage of the embodiments described herein is that they can be used in die-to-die mode or die-to-design mode. In one such example, comparing the design rendered contours to the image extracted contours is essentially die-to-design mode for contour comparison since contours from an image of a specimen are compared to contours rendered from a design. In addition or alternatively, the embodiments described herein may be configured for comparing contours extracted from different images generated from different locations on the specimen corresponding to the same portions of the design (e.g., the same within die locations, the same within reticle locations, etc.). In this manner, contours extracted from one image of a specimen can be compared to contours extracted from another image of the specimen, where all of the contours that are compared are extracted using a learning based model as described herein. Different comparisons may also be performed for the same specimen to detect different types of defects and/or to determine additional information about the defects. In this manner, the results of defect detection performed in die-to-die mode and die-to-design mode for a specimen may be combined to generate a single set of inspection results for the specimen.

In one embodiment, the one or more computer subsystems are configured for classifying the detected defects. The one or more computer subsystems may be configured to classify the detected defects using any suitable classification algorithm and/or method known in the art. In another embodiment, the one or more computer subsystems are configured for classifying the detected defects using an additional learning based model. For example, an advantage of the embodiments described herein is that the output of the detected events can be sent to a classification network that can classify the detected events as the user wants. The defects detected on the specimen can be classified using any of the learning based models described in the references, publications, and patent applications incorporated by reference as if fully set forth herein, The embodiments described herein provide a number of advantages in addition to those described further herein. For example, the embodiments provide pattern characterization and quantification within 1 pixel accuracy using end-to-end learning based algorithms. In addition, the embodiments described herein provide data driven and learning based methods for pattern characterization, quantification, and hot spot discovery to an accuracy of one pixel and are robust to OPC errors. This is an increasingly important requirement for metrology and inspection.

The embodiments described herein also do not require any heuristics and/or hand crafted algorithms for various pattern types, which are required by the currently used methods. For example, the image contour extraction based on deep learning described herein is much more robust as compared to non-deep learning based contour extraction algorithms. In particular, deep learning will automatically learn robust features (instead of coming up with hand-crafted features which may not be robust) based on the ground truth contour provided in the training examples. In addition, the embodiments described herein do not have challenges of currently used methods and systems including that edge pixels are not always connected, they require careful hand tweaking of parameters, and they are not robust at corners and junctions.

Furthermore, the embodiments described herein use algorithms that are robust and generalized to various pattern types, pattern density, layer types (memory or logic) and image modalities (e.g., optical, SEM, x-ray, etc.). For example, although some embodiments are described herein with respect to SEM images, the embodiments can be applied to image modalities other than electron beam (i.e., optical, x-ray, etc.). The embodiments described herein are therefore broadly applicable to many metrology, inspection, and other tool platforms. Moreover, the embodiments described herein can make use of alternate network topologies for both image contour extraction and design rendering which could produce the same or possibly better results.

Each of the embodiments of the system described herein may be further configured as described herein (e.g., more than one embodiment may be combined together into one single embodiment).

Another embodiment relates to a computer-implemented method for detecting defects in patterns formed on a specimen. The method includes acquiring images of patterns formed on a specimen by an imaging subsystem with one or more computer subsystems. The imaging subsystem is configured as described further herein. The method also includes generating simulated contours for the patterns based on a design for the specimen input to a first learning based model by the one or more computer subsystems. The simulated contours are expected contours of a defect free version of the patterns in the images of the specimen generated by the imaging subsystem. In addition, the method includes generating actual contours for the patterns in at least one of the acquired images of the patterns formed on the specimen input to a second learning based model by the one or more computer subsystems. One or more components are executed by the one or more computer subsystems. The one or more components include the first and second learning based models. The one or more computer subsystems and the one or more components are further configured as described herein. The method further includes comparing the actual contours to the simulated contours and detecting defects in the patterns formed on the specimen based on results of the comparing.

Each of the steps of the method may be performed as described further herein. The method may also include any other step(s) that can be performed by the imaging subsystem, computer subsystem(s), component(s), system(s), etc. described herein. The steps of the method are performed by various components (e.g., the first and second learning based models) and/or one or more computer subsystems as described further herein and which may be configured according to any of the embodiments described herein. In addition, the method described above may be performed by any of the system embodiments described herein.

Figure 8:
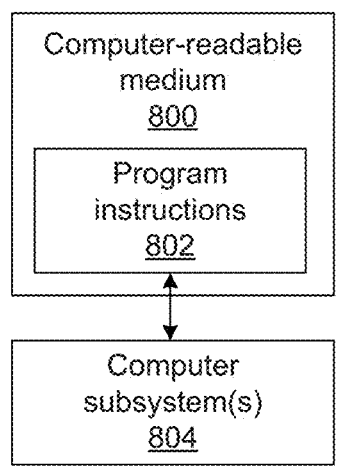
FIG. 8 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on one or more computer subsystems for performing a computer-implemented method for detecting defects in patterns formed on a specimen. One such embodiment is shown in FIG. 8. In particular, as shown in FIG. 8, non-transitory computer-readable medium 800 includes program instructions 802 executable on computer subsystem(s) 804. The computer-implemented method may include any step(s) of any method(s) described herein.

Program instructions 802 implementing methods such as those described herein may be stored on computer-readable medium 800. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer subsystem(s) 804 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, the defects detected in the patterns may be used to control and/or alter a fabrication process that was used to form the patterns on the specimen to thereby correct the fabrication process and prevent such pattern defects from occurring on other specimens. In one such example, information for the defects detected in the patterns may be used by the one or more computer subsystems described herein, another system (e.g., a fabrication system), or another method (e.g., a fabrication method) to determine how the fabrication process should be altered. Determining how the fabrication process should be altered may include determining one or more parameters of such a process such as the area on which the process is to be performed, the length of time that the process is to be performed, which chemicals or gases should be used in the process, etc. In this manner, the altered process can be used to print the patterns on other specimens in the fabrication process. Specimens patterned using the altered fabrication process may be inspected as described further herein to determine if the altered fabrication process has been appropriately corrected (i.e., the altered fabrication process did not print pattern defects on the specimens) and/or if additional corrections are needed.

Further modifications and alternative embodiments of various aspects of the invention will be apparent to those skilled in the art in view of this description. For example, methods and systems for detecting defects in patterns formed on a specimen are provided. Accordingly, this description is to he construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects in patterns formed on a specimen, comprising:
   an imaging subsystem comprising at least an energy source and a detector, wherein the energy source is configured to generate energy that is directed to a specimen, and wherein the detector is configured to detect energy from the specimen and to generate images responsive to the detected energy; and
   one or more computer subsystems configured for acquiring the images of patterns formed on the specimen; and
   one or more components executed by the one or more computer subsystems, wherein the one or more components comprise a first learning based model and a second learning based model, wherein the first and second learning based models are deep learning based models, wherein the first learning based model is configured for generating simulated contours for the patterns based on a design for the specimen input to the first learning based model by the one or more computer subsystems, wherein the simulated contours are expected contours of a defect free version of the patterns in the images of the specimen generated by the imaging subsystem, and wherein the second learning based model is configured for generating actual contours for the patterns in at least one of the acquired images of the patterns formed on the specimen input to the second learning based model by the one or more computer subsystems; and
   wherein the one or more computer subsystems are further configured for:
      comparing the actual contours to the simulated contours; and
      detecting defects in the patterns formed on the specimen based on results of the comparing.

2. The system of claim 1, wherein the results of the comparing comprise quantitative differences between dimensions of a first of the patterns in the design and the first of the patterns in the at least one of the acquired images of the patterns formed on the specimen determined based on differences between the actual and simulated contours, and wherein detecting the defects comprises applying a threshold to the quantitative differences between the dimensions.

3. The system of claim 1, wherein the results of the comparing comprise quantitative differences between the actual and simulated contours for each of the pixels of each of the patterns in the at least one of the acquired images.

4. The system of claim 1, wherein the one or more computer subsystems are further configured for detecting hot spots in the design based on the detected defects.

5. The system of claim 1, wherein the design input to the first learning based model does not include features of the design that will not be printed on the specimen.

6. The system of claim 1, wherein the first and second learning based models are adaptable to different pattern types.

7. The system of claim 1, wherein the first and second learning based models are adaptable to different patterns densities.

8. The system of claim 1, wherein the first and second learning based models are adaptable to patterns in different layer types.

9. The system of claim 1, wherein the first and second learning based models are adaptable to images generated by the imaging subsystem with one or more different imaging parameters.

10. The system of claim 1, wherein the one or more computer subsystems are further configured for training the first learning based model using a training data set comprising different portions of at least one training design for at least one training specimen and corresponding contour information extracted from training images of the at least one training specimen with a ground truth method.

11. The system of claim 1, wherein the one or more computer subsystems are further configured for training the second learning based model using a training data set comprising different training images generated by the imaging subsystem for at least one training specimen on which at least one training design was formed and corresponding contour information extracted from the different training images with a ground truth method.

12. The system of claim 1, wherein the second learning based model has a VGG network architecture.

13. The system of claim 1, wherein the second learning based model is further configured as a holistically-nested edge detection model.

14. The system of claim 1, wherein the first learning based model is further configured as a convolutional neural network.

15. The system of claim 1, wherein the first learning based model is further configured as a deep generative model using variational auto-encoders.

16. The system of claim 1, wherein the one or more computer subsystems are further configured for performing an additional comparing step in which the actual contours for the same patterns formed in different dies on the specimen are compared to each other and detecting defects in the same patterns based on results of the additional comparing step.

17. The system of claim 1, wherein the one or more computer subsystems are further configured for classifying the detected defects.

18. The system of claim 1, wherein the one or more computer subsystems are further configured for classifying the detected defects using an additional learning based model.

19. The system of claim 1, wherein the system is further configured as a metrology tool.

20. The system of claim 1, wherein the system is further configured as an inspection tool.

21. The system of claim 1, wherein the system is further configured as a defect review tool.

22. The system of claim 1, wherein the specimen comprises a wafer.

23. The system of claim 1, wherein the specimen comprises a reticle.

24. The system of claim 1, wherein the energy directed to the specimen comprises light, and wherein the energy detected from the specimen comprises light.

25. The system of claim 1, wherein the energy directed to the specimen comprises electrons, and wherein the energy detected from the specimen comprises electrons.

26. A non-transitory computer-readable medium, storing program instructions executable on one or more computer subsystems for performing a computer-implemented method for detecting defects in patterns formed on a specimen, wherein the computer-implemented method comprises:

acquiring images of patterns formed on a specimen generated by an imaging subsystem with the one or more computer subsystems, wherein the imaging subsystem comprises at least an energy source and a detector, wherein the energy source is configured to generate energy that is directed to the specimen, and wherein the detector is configured to detect energy from the specimen and to generate images responsive to the detected energy;

generating simulated contours for the patterns based on a design for the specimen input to a first learning based model by the one or more computer subsystems, wherein the simulated contours are expected contours of a defect free version of the patterns in the images of the specimen generated by the imaging subsystem;

generating actual contours for the patterns in at least one of the acquired images of the patterns formed on the specimen input to a second learning based model by the one or more computer subsystems, wherein one or more components are executed by the one or more computer subsystems, wherein the one or more components comprise the first and second learning based models, and wherein the first and second learning based models are deep learning based models;

comparing the actual contours to the simulated contours; and detecting defects in the patterns formed on the specimen based on results of the comparing.

27. A computer-implemented method for detecting defects in patterns formed on a specimen, comprising:

acquiring images of patterns formed on a specimen generated by an imaging subsystem with one or more computer subsystems, wherein the imaging subsystem comprises at least an energy source and a detector, wherein the energy source is configured to generate energy that is directed to the specimen, and wherein the detector is configured to detect energy from the specimen and to generate images responsive to the detected energy;

generating simulated contours for the patterns based on a design for the specimen input to a first learning based model by the one or more computer subsystems, wherein the simulated contours are expected contours of a defect free version of the patterns in the images of the specimen generated by the imaging subsystem;

generating actual contours for the patterns in at least one of the acquired images of the patterns formed on the specimen input to a second learning based model by the one or more computer subsystems, wherein one or more components are executed by the one or more computer subsystems, wherein the one or more components comprise the first and second learning based models, and wherein the first and second learning based models are deep learning based models;

comparing the actual contours to the simulated contours; and detecting defects in the patterns formed on the specimen based on results of the comparing.

* * * * *